US010120097B2

(12) United States Patent
Monteiro et al.

(10) Patent No.: US 10,120,097 B2
(45) Date of Patent: Nov. 6, 2018

(54) METHODS AND APPARATUS FOR MEASURING HYDROGEN SULFIDE IN DOWNHOLE FLUIDS

(71) Applicant: Baker Hughes Incorporated, Houston, TX (US)

(72) Inventors: Othon Do Rego Monteiro, Houston, TX (US); Devesh Kumar Agrawal, Houston, TX (US); Sankaran Murugesan, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 125 days.

(21) Appl. No.: 15/091,469

(22) Filed: Apr. 5, 2016

(65) Prior Publication Data

US 2017/0285211 A1    Oct. 5, 2017

(51) Int. Cl.
| | |
|---|---|
| *G01V 3/20* | (2006.01) |
| *G01N 27/12* | (2006.01) |
| *G01N 33/28* | (2006.01) |
| *E21B 49/08* | (2006.01) |
| *B82Y 30/00* | (2011.01) |

(52) U.S. Cl.
CPC ............... *G01V 3/20* (2013.01); *B82Y 30/00* (2013.01); *E21B 49/08* (2013.01); *G01N 27/128* (2013.01); *G01N 33/287* (2013.01); *E21B 2049/085* (2013.01)

(58) Field of Classification Search
CPC ... G01V 3/20; G01V 3/18; G01V 3/00; B82Y 30/00; E21B 49/08; E21B 49/00; G01N 27/128; G01N 27/12; G01N 27/00

USPC .......................................................... 436/28
See application file for complete search history.

(56) References Cited

U.S. PATENT DOCUMENTS

| | | |
|---|---|---|
| 5,304,492 A | 4/1994 | Klinkhammer |
| 6,020,207 A | 2/2000 | Liu |
| 6,507,401 B1 | 1/2003 | Turner et al. |
| 6,939,717 B2 | 9/2005 | Jiang et al. |
| 6,995,360 B2 | 2/2006 | Jones et al. |
| 7,025,138 B2 | 4/2006 | Kurkjian et al. |
| 7,231,819 B2 | 6/2007 | Jones et al. |

(Continued)

FOREIGN PATENT DOCUMENTS

EP    0656111 B1    2/2000

OTHER PUBLICATIONS

Shirsat et al, Polyaniline nanowires-gold nanoparticles hybrid network based chemiresistive hydrogen sulfide sensor,, Appl. Phys. Lett., 94, 2009, 083502-1 to 083502-3, (Year: 2009).*

(Continued)

*Primary Examiner* — Christine T Mui
(74) *Attorney, Agent, or Firm* — TraskBritt (57) ABSTRACT

A method of determining a concentration of hydrogen sulfide in a fluid comprises exposing a sensor to the fluid, the sensor comprising a pair of electrodes defining a gap therebetween and a sensing material bridging the gap between the electrodes, measuring a value of an electrical parameter of the sensor at an applied frequency of greater than about 10 kHz and a voltage of less than about 1.0 volt when the sensor is exposed to the fluid, and determining the concentration of hydrogen sulfide in the fluid based at least in part on the measured value of the electrical parameter. Related apparatuses and methods are also disclosed.

19 Claims, 4 Drawing Sheets

(56) References Cited

U.S. PATENT DOCUMENTS

| | | | |
|---|---|---|---|
| 7,251,384 | B2 | 7/2007 | da Silva Junior et al. |
| 7,253,004 | B2 | 8/2007 | Vossmeyer et al. |
| 7,395,704 | B2 | 7/2008 | DiFoggio |
| 7,423,258 | B2 | 9/2008 | DiFoggio et al. |
| 7,516,654 | B2 | 4/2009 | DiFoggio |
| 7,814,782 | B2 | 10/2010 | DiFoggio |
| 7,835,003 | B2 | 11/2010 | Jiang et al. |
| 7,959,864 | B2 | 6/2011 | Jiang et al. |
| 8,039,791 | B2 | 10/2011 | Dong et al. |
| 8,153,439 | B2 | 4/2012 | Zamborini et al. |
| 8,168,438 | B2 | 5/2012 | Zamborini et al. |
| 8,268,146 | B2 | 9/2012 | Jiang et al. |
| 8,379,207 | B2 | 2/2013 | DiFoggio et al. |
| 8,683,672 | B2 | 4/2014 | Deshusses et al. |
| 8,839,659 | B2 | 9/2014 | Xiao |
| 2002/0163639 | A1 | 11/2002 | Stephenson |
| 2008/0245960 | A1 | 10/2008 | Csutac |
| 2010/0050761 | A1 | 3/2010 | Lawrence et al. |
| 2012/0137764 | A1 | 6/2012 | Lawrence et al. |
| 2013/0056626 | A1 | 3/2013 | Shen et al. |
| 2014/0367092 | A1* | 12/2014 | Roberson ................ E21B 47/00 166/250.01 |
| 2015/0260668 | A1 | 9/2015 | Alam et al. |
| 2016/0011142 | A1 | 1/2016 | Serban et al. |
| 2016/0011161 | A1 | 1/2016 | Cobianu |

OTHER PUBLICATIONS

Mubeen et al, Sensitive Detection of H2S Using Gold Nanoparticle Decorated Single-Walled Carbon Nanotubes, Anal. Chem., 2010, 82, 250-527. (Year: 2010).*

Jin et al, Highly sensitive H2S gas sensors based on CuO-coated ZnSnO3 nanorods synthesized by thermal evaporation, Ceramics International, 2012, 38, 5973-5978. (Year: 2012).*

Chen et al., Reaction-Based Genetically Encoded Fluorescent Hydrogen Sulfide Sensors, Journal of the American Chemical Society, vol. 134, (2012), pp. 9589-9592.

Chen et al., A Red Amission Flourorescent Probe for Hydrogen Sulfide and its Application in Living Cells Imaging, Tetrahedron Letters, vol. 54, (2013), pp. 2980-2982.

Creek et al., Downhole Fluids Laboratory, Oilfield Review 21, No. 4, Winter 2009/2010, pp. 38-54.

Elsayed et al., Azide and Sulfonylazide Functionalized Fluorophores for the Selective and Sensitive Detection of Hydrogen Sulfide, Sensors and Actuators vol. B 207, (2015), pp. 987-994.

Kanan et al., Semiconductor Metal Oxide Based Sensors for Selective Gas Pollutant Detection, Sensors, vol. 9, (2009, (pp. 8158-8196.

Montoya et al., Development of Selective Calorimetric Probes for Hydrogen Sulfide Based on Nucleophilic Aromatic Substitution, The Journal of Organic Chemistry, vol. 78, (2013), pp. 6550-6557.

Montoya et al., Hydrogen Sulfide Deactivates Common Nitrobenzofuazan-Based Fluorescent Thiol Labeling Reagents, Analytical Chemistry, vol. 86, (2014), pp. 6032-6039.

Petrowiki, Nanotechnology in Hydrogen Sulfide Detection, http://petrowiki.org/Nanotechnology_in_hydrogen_sulfide_detection, last modified Oct. 28, 2015, 4 pages.

Rodriguez-Fernandez et al., Optical Fibre for Hydrogen Sulphide Monitoring in Mouth Air, Analytic Chimica Acta, vol. 471, (2002), pp. 13-23.

Wallace et al., A Colorimetric Response to Hydrogen Sulfide, Sensors and Actualtory vol. B 120, (2007), pp. 362-367.

Yuan et al., Reaction-Based Fluorescent Probe for Hydrogen Sulfide with Large Signal-to-Noise Ration in Living Cells and Tissues, Sensors and Actuators, vol. B 196, (2014), pp. 151-155.

Yusof et al., A Flow-Through Optical Fibre Reflectance Sensor for the Detection of Lead Ion Based on Immobilised Gallocynine, Sensors and Actuators vol. B 94, (2003), pp. 201-209.

* cited by examiner

METHODS AND APPARATUS FOR MEASURING HYDROGEN SULFIDE IN DOWNHOLE FLUIDS

TECHNICAL FIELD

Embodiments of the disclosure relate generally to chemiresistive sensors for use downhole, and to methods of using such chemiresistive sensors in conjunction with forming, enlarging, or maintaining a wellbore, as well as in production of hydrocarbons from subterranean formations.

BACKGROUND

Hydrogen sulfide is a toxic and corrosive gas. It can diffuse into downhole fluids, such as hydrocarbon fluids, produced from earth formations. Hydrogen sulfide corrodes infrastructure, reduces product value, and compromises safety and environmental compliance. Hence it is desirable to be able to detect the presence of hydrogen sulfide in the downhole fluids during early stages of producing reservoir assessment to determine suitable materials for components exposed to downhole fluids produced from wells drilled into such reservoirs. Detection of hydrogen sulfide in downhole fluids can also guide preventive treatments during production.

ASTM D5705 and UOP163 methods can be used for determining hydrogen sulfide levels. The ASTM D5705 method is based on the agitation of the sample and measurement of the gas concentration of hydrogen sulfide. Thus the method does not measure the hydrogen sulfide present in the liquid phase. The UOP 163 method is based on titration measurement of the liquid phase and relies on agitation of the sample under test at atmospheric pressure. A disadvantage of this test is that the method can lead to significant loss of entrained hydrogen sulfide, which may inaccurately represent an actual concentration of hydrogen sulfide in the liquid.

Chemiresistive sensors have been the subject of extensive research in the recent years. Conventional chemiresistive sensors are generally formulated and configured to sense a presence of an analyte in the vapor phase. However, to operate properly, such sensors require that the sensor be immersed in a vapor phase such that the only electrically conductive path of the sensor is through the sensing element. The electrical resistance of vapors is substantial, preventing any charge transfer through the vapor phase and ensuring that substantially all of the change transfer is through the sensing element of the chemiresistive sensor. Accordingly, such prior art chemiresistive sensors are not suitable for sensing an analyte present within a fluid (e.g., a liquid) of interest.

BRIEF SUMMARY

Embodiments disclosed herein include downhole chemiresistive sensor for determining a concentration of an analyte in a wellbore fluid, as well as related methods. For example, in accordance with one embodiment, a method of determining a concentration of hydrogen sulfide in a fluid comprises exposing a sensor to a fluid within a wellbore, the sensor comprising a pair of electrodes defining a gap therebetween and a sensing material bridging the gap between the electrodes, measuring a value of an electrical parameter of the sensor at an applied frequency of greater than about 10 kHz and a voltage of less than about 1.0 volt when the sensor is exposed to the fluid, and determining the concentration of hydrogen sulfide in the fluid based at least in part on the measured value of the electrical parameter.

In additional embodiments, a method of determining a concentration of hydrogen sulfide in a liquid within a wellbore comprises operably coupling, to at least a component of a downhole component, a sensor comprising a pair of electrodes and a sensing material electrically coupled to each electrode of the pair of electrodes, advancing the downhole component to a downhole location within a wellbore, measuring an electrical resistance across the sensing material while applying a voltage at a frequency greater than about 10 kHz responsive to exposure of the sensor to a liquid within the wellbore, and determining a concentration of hydrogen sulfide in the liquid based on measured electrical resistance.

In further embodiments, an apparatus for determining a concentration of hydrogen sulfide in a fluid comprises a carrier configured to be conveyed through a borehole penetrating an earth formation, a sensor disposed at the carrier and comprising a pair of electrodes defining a gap therebetween and a sensing material bridging the gap between the electrodes, the sensing material comprising metallic nanoparticles effective to reversibly adsorb hydrogen sulfide in a fluid, and a processor coupled to the sensor and configured to determine a concentration of hydrogen sulfide in the fluid based on a measured value of an electrical parameter through the sensing material between the electrodes.

DETAILED DESCRIPTION

Illustrations presented herein are not meant to be actual views of any particular material, component, or system, but are merely idealized representations that are employed to describe embodiments of the disclosure.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. In addition, the description provided below does not form a complete process flow for detecting a concentration of an analyte of a fluid within a subterranean formation, or to related chemiresistive sensors. Only those process acts and structures necessary to understand the embodiments of the disclosure are described in detail below. A person of ordinary skill in the art will understand that some process components (e.g., fiber optic cables, optical fibers, processors, pipelines, line filters, valves, temperature detectors, flow detectors, pressure detectors, and the like) are inherently disclosed herein and that adding various conventional process components and acts would be in accord with the disclosure. Additional acts or materials to determine a concentration of an analyte in a wellbore fluid with a downhole sensor may be performed by conventional techniques.

Disclosed are methods and apparatus for determining a concentration of hydrogen sulfide in a fluid within a wellbore (i.e., downhole). It is appreciated that determining the concentration of hydrogen sulfide inherently includes detecting a presence of the chemical in the fluid. According to the methods described herein, a sensor (e.g., a chemiresistive sensor) including two electrodes and a sensing material bridging a gap between the electrodes and configured to measure a property of the sensing material may be exposed to a fluid. As used herein, a chemiresistive sensor means and includes a material that exhibits a change in an electrical property (e.g., an electrical resistance, an electrical conductivity, an electrical impedance (e.g., a resistance and a permittivity), an electrical admittance, a capacitance, etc.) responsive to changes in a chemical environment proximate the sensor. As used herein, the terms "chemiresistive sensor" and "sensor" are used interchangeably. The sensing material comprises metallic nanoparticles that are effective to reversibly adsorb hydrogen sulfide present in the fluid. Adsorption of hydrogen sulfide on the sensing material of the chemiresistive sensor results in a change in an electrical parameter (or property) of the chemiresistive sensor, which may be used to determine the concentration of hydrogen sulfide in the fluid. As used herein, the terms parameter and property are used interchangeably and may refer to, for example, an electrical resistivity, an electrical conductivity, electrical impedance, electrical admittance, or a capacitance.

Advantageously, the method directly detects hydrogen sulfide in the liquid phase. Contrary to conventional chemiresistive sensors that are only effective for measuring a concentration of an analyte in a vapor phase, the chemiresistive sensors described herein may be used to determine a concentration of an analyte in the liquid phase. Further the method can be used in various downhole environments including high pressure and high temperature conditions and are compatible with fluids having different levels of salinity.

Figure 1:
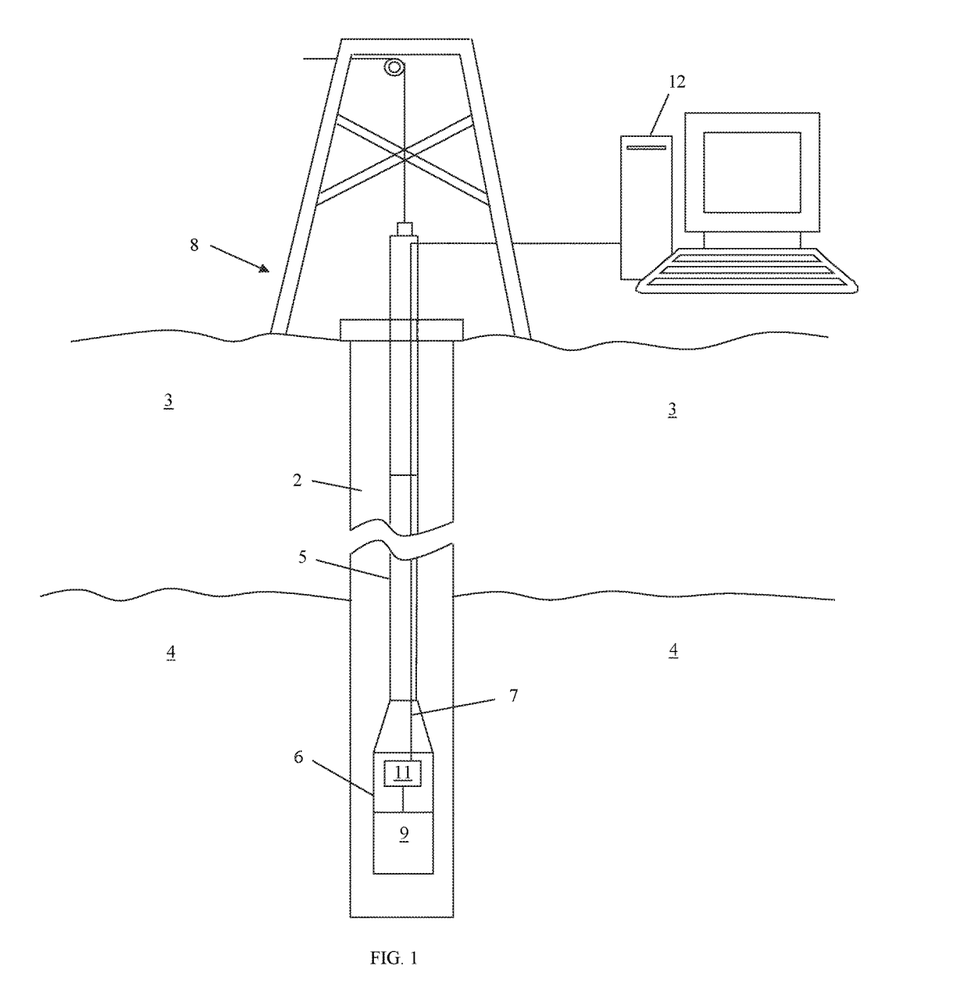
FIG. 1 is a schematic diagram of a downhole tool disposed in a borehole penetrating the earth, according to an embodiment of the disclosure.

FIG. 1 illustrates a cross-sectional view of an example embodiment of a downhole tool 6 disposed in a borehole 2 penetrating the earth 3, which may include an earth formation (i.e., a subterranean formation) 4 comprising a hydrocarbon-bearing reservoir. The downhole tool 6 may include a sensor 9 configured to determine a concentration of hydrogen sulfide in a downhole fluid. Nonlimiting examples of the fluid include a borehole fluid such as drilling, completion, workover and production fluids. The downhole tool 10 is advanced downhole through the borehole 2 by a carrier 5. A rig 8 is configured to conduct various well operations. Downhole electronics 11 are configured to operate the sensor 9, process measurement data obtained downhole, and/or act as an interface with telemetry element 7 to communicate data or commands between downhole components and a computer processing system 12 disposed at the surface of the earth 3. System operation and data processing operations may be performed by the downhole electronics 11, the computer processing system 12, or a combination thereof. The sensor 9 may be operated continuously or at discrete selected depths in the borehole 2. The downhole tool 6 may include openings (or perforations, not shown) to allow fluid, for example, a hydrocarbon fluid from earth formation 4, to flow through the downhole tool 6 and contact the sensor 9.

The carrier 5 may include any device, device component, downhole component, or combination of downhole components that may be used to convey, house, support or otherwise facilitate the use of another device, device component, combination of devices, media and/or member. By way of nonlimiting example, the carrier 5 may include a tubular string of the coiled tubing type, of the jointed pipe type and any combination or portion thereof, wireline, wireline sondes, slickline, slickline sondes, drop shots, bottom-hole assemblies (BHAs), drill string inserts, modules, internal housings and substrate portions thereof. In some embodiments, the carrier 5 may include an armored wireline, which can also act as telemetry element 7 to provide communications with the computer processing system 12.

Figure 2:
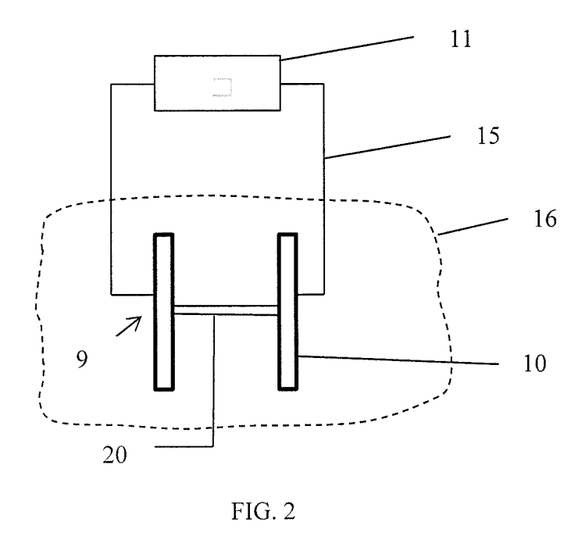
FIG. 2 schematically illustrates a sensor configured to determine the concentration of hydrogen sulfide in a fluid, according to embodiments of the disclosure.

Referring to FIG. 2, the sensor 9 includes a pair of electrodes 10 defining a gap therebetween and a sensing material 20 bridging the gap between the electrodes 10. The sensor 9 may be operably coupled to the downhole electronics 11 via wires 15 and can be used to determine a concentration of hydrogen sulfide within fluid 16 with which the sensor 9 is in direct physical contact.

The electrodes 10 may comprise conductive materials such as gold, nickel, platinum, palladium or other metals, alloys thereof, or other suitable metals or alloys not adversely affected by exposure to hydrogen sulfide. The electrodes 10 may be formed on a dielectric layer by methods such as chemical vapor deposition (including atomic layer deposition, physical vapor deposition, electrochemical deposition, screen printing, or other known deposition methods. The dielectric layer may include oxides, nitrides, oxynitrides, carbides, or a combination comprising at least one of the foregoing. In some embodiments, the electrodes are formed directly on a dielectric substrate, wherein the dielectric substrate comprises a dielectric material as disclosed herein.

The electrodes 10 may be substantially mutually parallel and may be separated, by way of nonlimiting example, by a gap of about 100 nanometers to about 500 microns, or about 500 nanometers to about 100 microns. In some embodiments, the material bridging the gap between the electrodes 10 comprises metallic nanoparticles configured and formulated to reversibly adsorb hydrogen sulfide in the fluid 16. Adsorption of hydrogen sulfide onto the metallic nanoparticles may alter one or more electrical properties of the sensor 9. A concentration of hydrogen sulfide in the fluid 16 may be determined based, at least in part, on changes of the electrical properties of the sensor 9.

As used herein, the term "nanoparticles" means and includes particles with an average particle size (largest average dimension) of about 1 nanometer to less than about 1 micrometer. In some embodiments, the nanoparticles have an average particle size of less than about 1 micrometer, and more specifically a largest average dimension less than or equal to about 500 nanometers, and still more specifically less than or equal to about 250 nanometers, where particle sizes of greater than about 250 nanometers to less than about 1 micron are also referred to in the art as "sub-micron sized particles." The nanoparticles may include nanorods, nanofibers, nanowires, porous nanoparticles, and other nanoporous structures. As used herein, the term "average particle size" means and includes a particle size based on a number of average particle size measurements, which can be routinely obtained by laser light scattering methods such as static light scattering (SLS) or dynamic light scattering (DLS). Also in some embodiments, the nanoparticles have a dimensional aspect ratio of greater than about 1, such as greater than about 10, or greater than about 50. Nanoparticles may be any shape including spherical, angular, and polyhedral.

The sensing material 20 may include metallic nanoparticles comprising gold, silver, copper, a gold alloy, a silver alloy, a copper alloy, or a combination comprising at least one of the foregoing. The metallic nanoparticles may be directly grown between the electrodes 10 by methods such as physical vapor deposition (PVD). In another embodiment, the metallic nanoparticles may be deposited between the electrodes 10 using dielectrophoresis. Alternatively, the metallic nanoparticles are deposited on a substrate, a permeable structure, or a combination comprising at least one of the foregoing.

The sensor 9 may be configured to detect at least one electrical property of the sensing material 20. When an electrical property such as electric resistance is measured, the sensing material 20 may comprise metallic nanoparticles interdispersed in a permeable structure. Illustrative permeable structures of the sensing material 20 include a conductive carbon network, a conductive polymer matrix, or a combination comprising at least one of the foregoing. Metallic nanoparticles can be infiltrated into the permeable structure by chemical vapor infiltration, thermal evaporation, electrophoretic deposition, plating or other solution-based methods. As used herein, conductive materials include semiconductive materials.

The sensing material 20 may include conductive carbon including, for example, carbon nanotubes, graphene, other conductive carbon materials, and combinations thereof. Carbon nanotubes may be functionalized with conductive nanoparticles, such as with one or more of gold, nickel, platinum, or palladium. In some embodiments, the sensing material 20 comprises a carbon nanotube network. Conductive polymers, also known as intrinsically conducting polymers, are organic polymers that conduct electricity. Illustrative conductive polymers include polyanilines, polyfluorenes, polyphenylenes, polypyrenes, polyazulenes, polynaphthalenes, polypyrroles, polycarbazoles, polyindoles, polyazepines, polythiophenes, poly(3,4-ethylenedioxythiophene), poly(p-phenylene sulfide), polyacetylenes, poly(p-phenylene vinylene), or a combination comprising at least one of the foregoing. A nonlimiting example of a conductive polymer matrix includes a polymer mat.

In one embodiment, alumina membranes can be prepared by anodization and followed by deposition of metallic nanoparticles (e.g., gold, nickel, platinum, palladium, or combinations thereof) by physical vapor deposition or chemical vapor deposition. Monodispersed polystyrene spheres can also be used to prepare nanorods as a template to grow metallic nanoparticles or a substrate onto which metallic nanoparticles are deposited.

Figure 3:
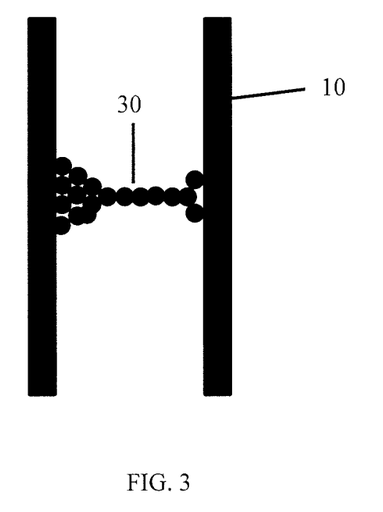
FIG. 3 schematically illustrates a sensor for measuring hydrogen sulfide in downhole fluids wherein the sensing material comprises metallic nanoparticles, according to other embodiments of the disclosure.
Figure 4:
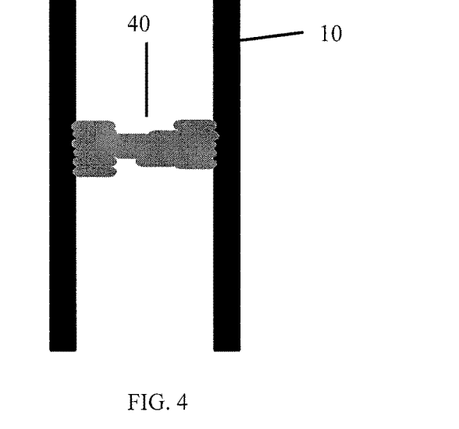
FIG. 4 schematically illustrates a sensor for measuring hydrogen sulfide in downhole fluids wherein the sensing material comprises metallic nanorods, according to yet other embodiments of the disclosure.
Figure 5:
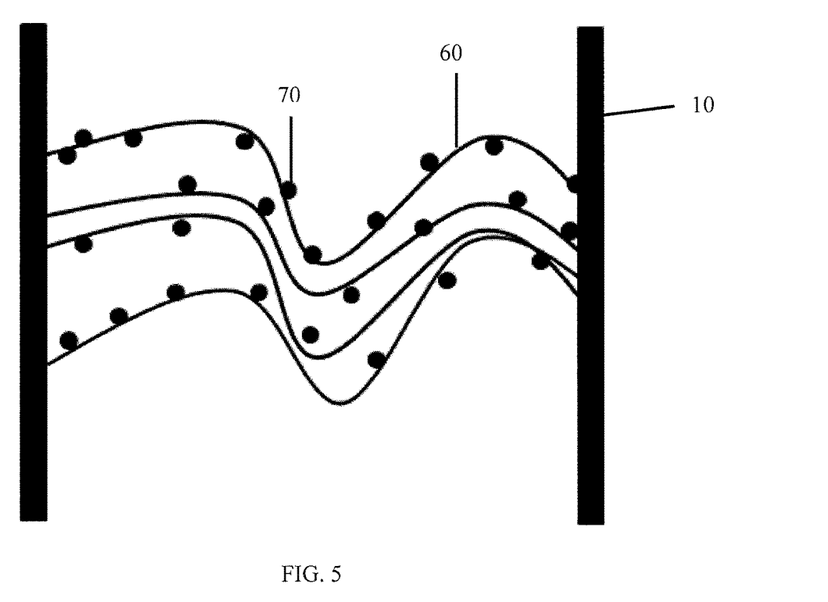
FIG. 5 schematically illustrates a sensor for measuring hydrogen sulfide in downhole fluids wherein the sensing material comprises metallic nanoparticles infiltrated in a network of carbon nanotubes, according to embodiments of the disclosure.
Figure 6:
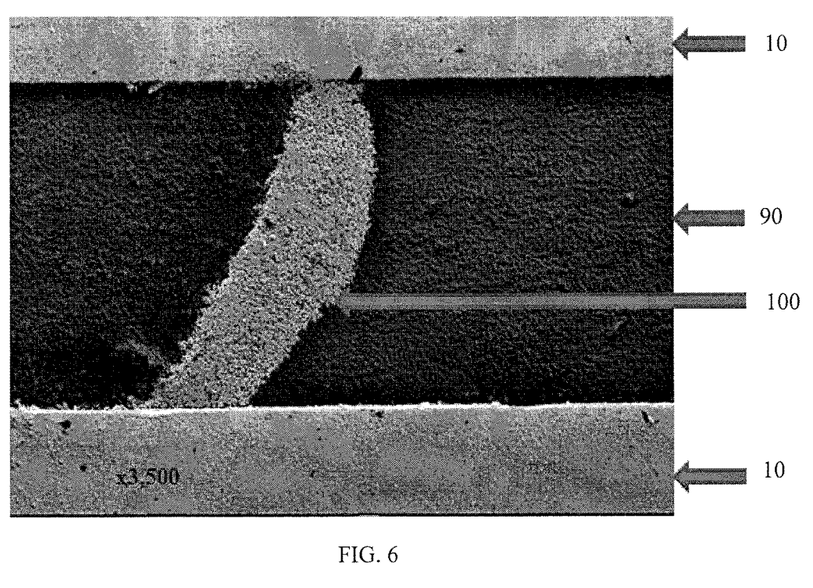
FIG. 6 is a scanning electron microscope (SEM) image of a sensor for measuring hydrogen sulfide in downhole fluids, wherein the sensing material comprises metallic nanoparticles disposed on a dielectric substrate.

FIG. 3 through FIG. 6 illustrate sensors according to various embodiments of the disclosure. In FIG. 3, the sensor includes electrodes 10 and metallic nanoparticles 30 bridging a gap between the electrodes 10. In FIG. 4, the sensor contains electrodes 10 and metallic nanorods 40 bridging a gap between the electrodes 10. In FIG. 5, the sensing material between the electrodes 10 comprises metallic nanoparticles 70 interdispersed in a carbon nanotube network 60. In FIG. 6, the metallic nanoparticles 100 are deposited on and between a substrate 90 forming a bridge between electrodes 10.

A method of determining a concentration of hydrogen sulfide in a fluid comprises exposing a sensor to the fluid, measuring the value of an electrical parameter of the sensor, and comparing the measured value of the electrical parameter to a predetermined baseline value or a previously determined calibration curve of the electrical parameter of the sensor thereby determining the concentration of hydrogen sulfide in the fluid. By way of nonlimiting example, the computer processing system 12 (FIG. 1) may be operably coupled to memory including, for example, a look-up table correlating an electrical parameter of the sensing material 20 (FIG. 2) measured by the sensor 9 (FIG. 2) to a concentration of hydrogen sulfide in the fluid to which the sensor 9 is exposed. In some embodiments, the electrical parameter is an electrical resistivity or an electrical conductivity. However, the disclosure is not so limited and in other embodiments, the electrical parameter may include an inductance or a capacitance. In some embodiments, such as where the electrical parameter comprises an inductance, the sensor 9 may include an inductor (e.g., a coil of wire).

Adsorption of $H_2S$ onto a surface of the sensing material 20 (FIG. 2) may alter at least one electrical property (e.g., an electrical resistance) of the sensor 9 (FIG. 2). When the surface of the sensing material 20 is exposed to the liquid, equilibrium is established between a concentration of adsorbed $H_2S$ and a concentration of dissolved $H_2S$ in the liquid. The resistivity (and the inductance) of the sensor 9 across the sensing material 20 may be related to the concentration of adsorbed $H_2S$, and therefore the concentration of dissolved $H_2S$. The relationship between the concentration of adsorbed $H_2S$ (also referred to as surface coverage) and the concentration of dissolved $H_2S$ is usually referred to as the adsorption isotherm, according to Equation (1) below.

$$H_2S_{ads} \propto H_2S_{liq} \qquad (1),$$

wherein $H_2S_{ads}$ is the concentration of $H_2S$ adsorbed onto the sensing material 20 and $H_2S_{liq}$ is the concentration of the hydrogen sulfide in the liquid phase. Accordingly, since a concentration of hydrogen sulfide adsorbed on the sensor 9 is directly proportional to a concentration of hydrogen sulfide dissolved in a liquid in contact with the sensor 9 and the electrical parameter of the sensing material 20 is correlated to a concentration of hydrogen sulfide adsorbed on the sensing material 20, the concentration of hydrogen sulfide may be determined based on at least one measured electrical parameter across the sensing material 20. In some embodiments, a value of the electrical parameter across the sensing material 20 may be determined at a plurality of known concentrations of an analyte in a laboratory under a controlled environment. For each concentration of the analyte in the fluid, the electrical parameter may be stored in a memory associated with the computer processing system 12 (FIG. 1) such as in a look-up table or a calibration curve correlating the concentration of the analyte in a fluid to the electrical parameter. A value of the measured parameter when the sensor 9 (FIG. 2) is located downhole may be compared to the calibration curve or a look-up table stored in, for example, a memory of the computer processing system 12 (FIG. 1) to determine a concentration of hydrogen sulfide in the downhole fluid.

Fluids in the downhole environments often contain various ions, which may interfere with at least one electrical parameter (e.g., an electrical resistivity) of a sensor in contact with the fluid. Applicants have found that when the electrical resistivity of the sensor is measured at particular frequency and voltage ranges, the concentration of hydrogen sulfide in the fluids can be reliably determined regardless of the salinity of the fluid. The suitable frequency is greater than about 10 kHz, greater than about 100 kHz, or greater than about 1 MHz. The upper end limit of the frequency range is not particularly limited and can be, for example, about 300 MHz. An upper end of a suitable voltage may be less than about 1 volt. The lower end of the voltage can be about 500 millivolt, about 100 millivolt, about 50 millivolt, about 10 millivolt, or about 5 millivolt. The suitable voltage range can also be between any of the two end limits described herein.

Chemiresistive sensors of the prior art, however, have been unable to measure a concentration of an analyte in a liquid because they do not operate at such high frequencies and low voltages. Such chemiresistive sensors are configured to transmit a DC voltage or current across an electrode of the sensor and determine the resistance across the sensor based on Ohms law (i.e., V=IR, wherein V is the voltage, I is the current, and R is the resistance). However, the DC voltage or DC current at which such sensors are configured to operate may induce ionic flow through a liquid. Such ionic flow may interfere with a resistance between electrodes of the sensor and may therefore, not be suitable for determining a concentration of an analyte in the fluid.

Without wishing to be bound by any particular theory, it is believed that measuring the at least one electrical parameter (e.g., an electrical conductivity, an electrical resistivity, an impedance, etc.) at a frequency greater than about 10 kHz and at a voltage less than about 1 volt facilitates accurate measurement of the at least one electrical parameter and correlation thereof to a concentration of hydrogen sulfide in a liquid. Since the sensors 9 (FIG. 2) described herein are operated at a higher frequency and a lower voltage than sensors of the prior art, they may be used to accurately determine a concentration of an analyte (e.g., hydrogen sulfide) in a liquid. It is believed that at the higher frequencies, ions within the fluid exhibit substantially no net movement and therefore, do not substantially interfere with measurement of the electrical property between the electrodes 10 (FIG. 2). However, since electron transport through the sensing material 20 (FIG. 2) is a function of change transport through the sensing material 20 (such as by electron hopping or tunneling phenomena), the electrical resistivity of the sensing material 20 may be measured and unaffected by the higher frequencies and lower voltages.

In support of the disclosure herein, various analysis components may be used, including a digital and/or an analog system. For example, the downhole electronics 11, the computer processing system 12, or the sensor 9 may include digital and/or analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

All ranges disclosed herein are inclusive of the endpoints, and the endpoints are independently combinable with each other. As used herein, "combination" is inclusive of blends, mixtures, alloys, reaction products, and the like. All references are incorporated herein by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." The modifier "about" used in connection with a quantity is inclusive of the stated value and has the meaning dictated by the context (e.g., it includes the degree of error associated with measurement of the particular quantity).

Additional nonlimiting example embodiments of the disclosure are described below.

Embodiment 1: A method of determining a concentration of hydrogen sulfide in a fluid, the method comprising: exposing a sensor to a fluid within a wellbore, the sensor comprising a pair of electrodes defining a gap therebetween and a sensing material bridging the gap between the electrodes; measuring a value of an electrical parameter of the sensor at an applied frequency of greater than about 10 kHz and a voltage of less than about 1.0 volt when the sensor is exposed to the fluid; and determining the concentration of hydrogen sulfide in the fluid based at least in part on the measured value of the electrical parameter.

Embodiment 2: The method of Embodiment 1, wherein determining the concentration of hydrogen sulfide in the fluid comprises comparing the measured value of the electrical parameter to a previously determined calibration curve or set of values of the electrical parameter of the sensor and correlating the measured value to the previously determined calibration curve or set of values.

Embodiment 3: The method of Embodiment 1 or Embodiment 2, wherein the fluid is a liquid.

Embodiment 4: The method of any one of Embodiments 1 through 3, further comprising selecting the electrical parameter to comprise electrical resistance.

Embodiment 5: The method of any one of Embodiments 1 through 4, wherein: the frequency is greater than about 100 kHz; and the voltage is between about 5 millivolts and about 1 volt.

Embodiment 6: The method of any one of Embodiments 1 through 4, wherein: the frequency is between about 100 kHz and about 300 kHz; and the voltage is between about 100 millivolts and about 1 volt.

Embodiment 7: The method of any one of Embodiments 1 through 6, further comprising selecting the sensing material to comprise metallic nanoparticles that reversibly adsorb or absorb hydrogen sulfide in the fluid.

Embodiment 8: The method of Embodiment 7, further comprising selecting the metallic nanoparticles to comprise gold, silver, copper, a gold alloy, a silver alloy, a copper alloy, or a combination comprising at least one of the foregoing.

Embodiment 9: The method of any one of Embodiments 1 through 8, further comprising selecting the sensing material to comprise metallic nanoparticles interdispersed in a conductive carbon network, a conductive polymer matrix, or a combination comprising at least one of the foregoing.

Embodiment 10: The method of Embodiment 9, further comprising infiltrating the metallic nanoparticles by chemical vapor infiltration, thermal evaporation, dielectrophoretic deposition, plating, or a combination comprising at least one of the foregoing.

Embodiment 11: The method of Embodiment 9, further comprising selecting the conductive polymer matrix to comprise polyaniline, poly(fluorene), polyphenylene, polypyrene, polyazulene, polynaphthalene, poly(pyrrole), polycarbazole, polyindole, polyazepine, poly(thiophene), poly(3, 4-ethylenedioxythiophene), poly(p-phenylene sulfide), poly (acetylene), poly(p-phenylene vinylene), or a combination comprising at least one of the foregoing.

Embodiment 12: The method of any one of Embodiments 1 through 6, further comprising selecting the sensing material to comprise a metallic film having a thickness below about 100 nm.

Embodiment 13: The method of any one of Embodiments 1 through 12, further comprising selecting the electrical parameter to comprise electrical impedance.

Embodiment 14: The method of any one of Embodiments 1 through 13, further comprising disposing the sensor in the wellbore penetrating an earth formation comprising a source of the fluid.

Embodiment 15: The method of Embodiment 14, further comprising selecting the carrier to comprise a wireline, a slickline, a drill string or coiled tubing.

Embodiment 16: A method of determining a concentration of hydrogen sulfide in a liquid within a wellbore, the method comprising: operably coupling, to at least a component of a downhole component, a sensor comprising a pair of electrodes and a sensing material electrically coupled to each electrode of the pair of electrodes; advancing the downhole component to a downhole location within a wellbore; measuring an electrical resistance across the sensing material while applying a voltage at a frequency greater than about 10 kHz responsive to exposure of the sensor to a liquid within the wellbore; and determining a concentration of hydrogen sulfide in the liquid based on measured electrical resistance.

Embodiment 17: The method of Embodiment 16, further comprising selecting the sensing material to comprise gold nanoparticles interdispersed in a network of carbon nanotubes.

Embodiment 18: The method of Embodiment 16 or Embodiment 17, further comprising measuring the electrical resistance while applying a voltage less than about 1.0 V across the pair of electrodes.

Embodiment 19: An apparatus for determining a concentration of hydrogen sulfide in a fluid, the apparatus comprising: a carrier configured to be conveyed through a borehole penetrating an earth formation; a sensor disposed at the carrier and comprising a pair of electrodes defining a gap therebetween and a sensing material bridging the gap between the electrodes, the sensing material comprising metallic nanoparticles effective to reversibly adsorb hydrogen sulfide in a fluid; and a processor coupled to the sensor and configured to determine a concentration of hydrogen sulfide in the fluid based on a measured value of an electrical parameter through the sensing material between the electrodes.

Embodiment 20: The apparatus of Embodiment 19, wherein the sensor is configured to measure the electrical parameter under electrical stimulation at a frequency greater than about 10 kHz and a voltage of less than about 1 volt to the sensor.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A method of determining a concentration of hydrogen sulfide in a liquid, the method comprising:
    exposing a sensor to a liquid within a wellbore, the sensor comprising a pair of electrodes, major surfaces of the electrodes of the pair of electrodes opposing each other and defining a gap therebetween and a sensing material bridging the gap between the major surfaces of the electrodes;
    applying, to the sensor, a voltage of less than about 1.0 volt at a frequency greater than about 10kHz;
    while applying the voltage, measuring a value of an electrical parameter of the sensor while the sensor is exposed to the liquid; and
    determining the concentration of hydrogen sulfide in the liquid based at least in part on the measured value of the electrical parameter.

2. The method of claim 1, wherein determining the concentration of hydrogen sulfide in the liquid comprises comparing the measured value of the electrical parameter to a previously determined calibration curve or set of values of the electrical parameter of the sensor and correlating the measured value to the previously determined calibration curve or set of values.

3. The method of claim 1, further comprising selecting the electrical parameter to comprise electrical resistance.

4. The method of claim 1, further comprising:
    selecting the frequency to be greater than about 100 kHz; and
    selecting the voltage to be between about 5 millivolts and about 1 volt.

5. The method of claim 1, further comprising:
    selecting the frequency to be between about 100 kHz and about 300 kHz; and
    selecting the voltage to be between about 100 millivolts and about 1 volt.

6. The method of claim 1, further comprising selecting the sensing material to comprise metallic nanoparticles that reversibly adsorb or absorb hydrogen sulfide in the liquid.

7. The method of claim 6, further comprising selecting the metallic nanoparticles to comprise gold, silver, copper, a gold alloy, a silver alloy, a copper alloy, or combinations thereof.

8. The method of claim 1, further comprising selecting the sensing material to comprise metallic nanoparticles interdispersed in a conductive carbon network, a conductive polymer matrix, or a combination thereof.

9. The method of claim 8, further comprising infiltrating the metallic nanoparticles by chemical vapor infiltration, thermal evaporation, dielectrophoretic deposition, plating, or combinations thereof.

10. The method of claim 8, further comprising selecting the conductive polymer matrix to comprise polyaniline, poly(fluorene), polyphenylene, polypyrene, polyazulene, polynaphthalene, poly(pyrrole), polycarbazole, polyindole, polyazepine, poly(thiophene), poly(3,4-ethylenedioxythiophene), poly(p-phenylene sulfide), poly(acetylene), poly(p-phenylene vinylene), or combinations thereof.

11. The method in claim 1, further comprising selecting the sensing material to comprise a metallic film having a thickness below about 100 nm.

12. The method of claim 1, further comprising selecting the electrical parameter to comprise electrical impedance.

13. The method of claim 1, further comprising disposing the sensor in the wellbore penetrating an earth formation comprising a source of the liquid.

14. The method of claim 1, wherein exposing a sensor to a liquid within a wellbore comprises advancing a carrier including the sensor to a downhole location within the wellbore, wherein the carrier comprises a wireline, a slickline, a drill string, or coiled tubing.

15. A method of determining a concentration of hydrogen sulfide in a liquid within a wellbore, the method comprising:
    operably coupling, to at least a component of a downhole component, a sensor comprising a pair of electrodes and a sensing material electrically coupled to each electrode of the pair of electrodes, major surfaces of the electrodes of the pair of electrodes opposing each other by a gap within which the sensing material is located;
    advancing the downhole component to a downhole location within a wellbore;
    applying, to the sensor, a voltage of less than about 500 millivolts at a frequency greater than about 10 kHz;
    measuring an electrical resistance across the sensing material responsive to exposure of the sensing material to a liquid within the wellbore; and
    determining a concentration of hydrogen sulfide in the liquid based on measured electrical resistance.

16. The method of claim 15, further comprising selecting the sensing material to comprise gold nanoparticles interdispersed in a network of carbon nanotubes.

17. The method of claim 15, further comprising measuring the electrical resistance while applying a voltage less than about 1.0 V across the pair of electrodes.

18. The method of claim 15, further comprising selecting the sensing material to comprise a carbon network.

19. The method of claim 15, further comprising selecting the sensing material to comprise metallic nanorods bridging a gap between the electrodes of the pair of electrodes, the metallic nanorods comprising metallic nanoparticles selected from the group consisting of gold, nickel, platinum, palladium, and combinations thereof.

* * * * *